United States Patent [19]
Rabinovitz et al.

[11] Patent Number: 4,926,875
[45] Date of Patent: May 22, 1990

[54] IMPLANTABLE AND EXTRACTABLE BIOLOGICAL SENSOR PROBE

[75] Inventors: Raphael S. Rabinovitz; Craig J. Hartley, both of Houston, Tex.

[73] Assignee: Baylor College of Medicine, Houston, Tex.

[21] Appl. No.: 199,163

[22] Filed: May 26, 1988

Related U.S. Application Data

[63] Continuation-in-part of Ser. No. 147,368, Jan. 25, 1988, abandoned.

[51] Int. Cl.$^5$ .............................................. A61B 5/02
[52] U.S. Cl. ................................. 128/691; 128/662.04
[58] Field of Search .............................. 128/691–692, 128/668, 661.07–661.08, 662.04–662.06, 784–786, 642, 334 R, 335.5, 419 P

[56] References Cited

U.S. PATENT DOCUMENTS

| 3,124,132 | 3/1964 | Sullivan . | |
| 3,605,726 | 9/1971 | Williams et al. | 128/691 |
| 3,661,146 | 5/1972 | Peronneau . | |
| 3,921,622 | 11/1975 | Cole . | |
| 3,955,560 | 5/1976 | Stein et al. . | |
| 3,977,247 | 8/1976 | Hassler . | |
| 4,313,443 | 2/1982 | Lund | 128/642 |
| 4,355,643 | 10/1982 | Laughlin | 128/663 |
| 4,419,999 | 12/1983 | May, Jr. et al. | 128/691 |
| 4,442,844 | 4/1984 | Navach | 128/663 |
| 4,541,433 | 9/1985 | Baudino | 128/668 |
| 4,602,624 | 7/1986 | Naples et al. . | |

FOREIGN PATENT DOCUMENTS 217689 4/1987 France .

OTHER PUBLICATIONS

Matre et al., "Continuous Measurement of Aortic Blood Velocity, after Cardiac Surgery, by Means of an Extractable Doppler Ultrasound Probe", *J. Biomec. Eng.*, vol. 4, 1985, pp. 84–88.
Keagy et al., "Constant Postoperative Monitoring of Cardiac Output after Correction of Congenital Heart Defects", *J. Thorac. Cardiovasc. Surg.*, 1987;93;658-64.
Svennevig et al., "Continuous Monitoring of Cardiac Output Postoperatively Using an Implantable Doppler Probe", *Scand. J. Cardiovasc. Surg.*, 20:145-149, 1986.
Payen et al., "Comparison of Perioperative and Postoperative Phasic Blood Flow in Aortocoronary Bypass Grafts by Means of Pulsed Doppler Echocardiography with Implantable Microprobes", *Coronary Artery Surgery*, vol. 74, (Suppl. III), Nov. 1986, 111-61-111-67.
Derwent's Abst. No. 80-A1750 D/02, SU 733643.
Derwent's Abst. No. 81-G8361 E/23, SU 856437.

Primary Examiner—Angela D. Sykes
Attorney, Agent, or Firm—Vaden, Eickenroht, Thompson & Boulware

[57] ABSTRACT

This invention is an implantable, extractable probe for biological sensors which has a stable attachment to different sizes of vessels or organs and is safety and easily removed from the patient. The body of the probe is made up of a biocompatible flexible material. The probe encircles the vessel or organ to be monitored by suture attachment of the probe body to itself. A release wire within the probe body holds the suture in place until time for the removal of the probe from the body. The probe is then extracted without a surgical procedure.

13 Claims, 5 Drawing Sheets

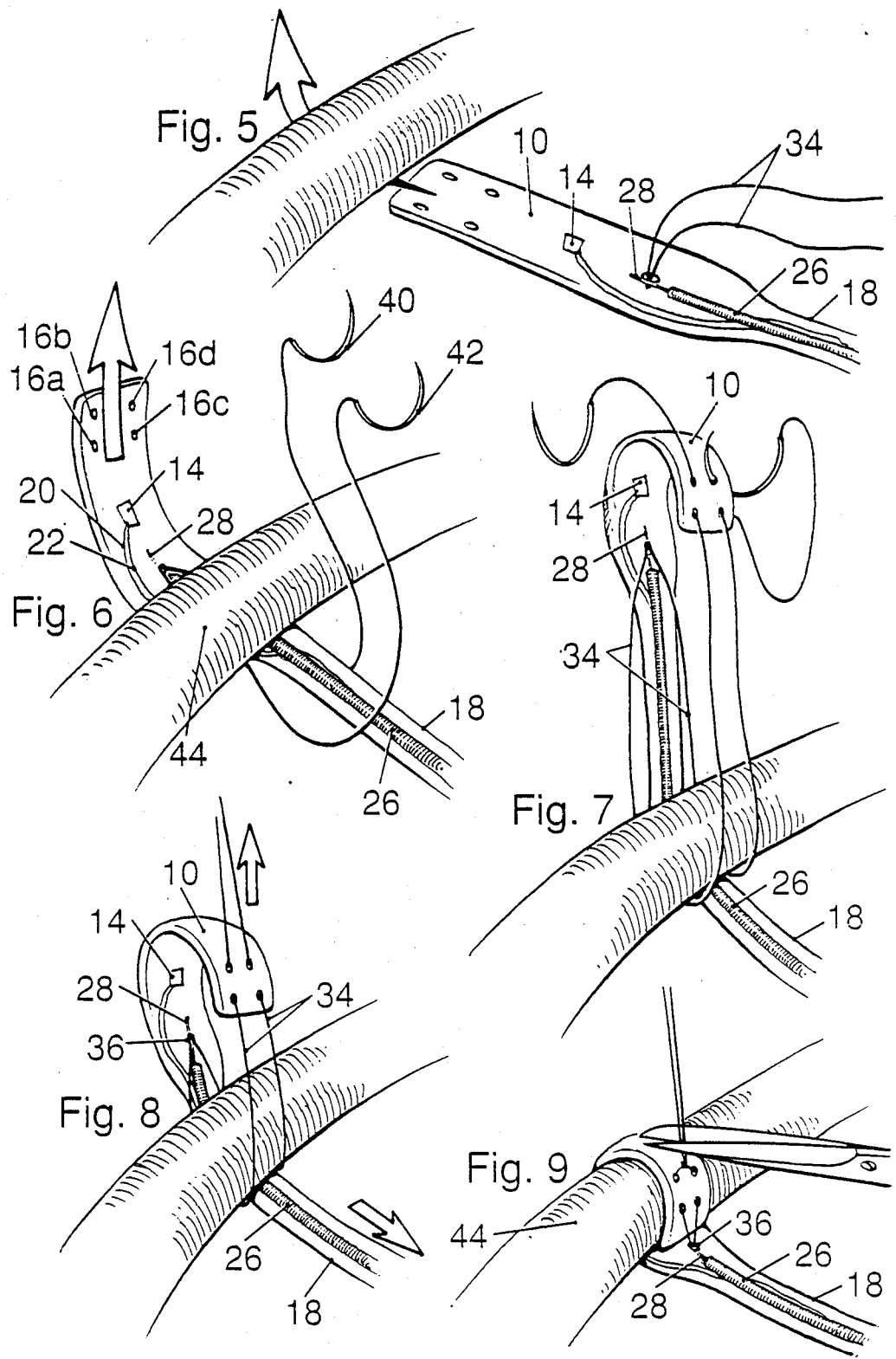

IMPLANTABLE AND EXTRACTABLE BIOLOGICAL SENSOR PROBE

ORIGIN OF THE INVENTION

The invention described herein was made using federal funds and may be manufactured or used by or for the government of the United States of America for governmental purposes without payment of any royalties thereon or therefor.

This application is a continuation-in-part of U.S. Ser. No. 07/147,368 filed on Jan. 25, 1988, now abandoned.

BACKGROUND OF THE INVENTION

Measuring the responses of organs in a body is becoming more common with the development of small implantable biological sensors. For example, the continuous measurement of blood flow in vessels, particularly in postoperative cases, is desirable for the evaluation of vascular reconstructive operations, organ transplants and other medical procedures. Various blood flow velocity (and diameter) sensors have been developed including electromagnetic type flow meters and pulsed ultrasonic Doppler transducers consisting of a single piezoelectric crystal acting as an ultrasonic transmitter and receiver. The flow velocity sensors, particularly the Doppler flow probe, are very small and can be used inside a patient.

The small flow probes can be used to monitor continuously blood flow in a patient for a period of time, postoperative or otherwise. The sensor or probe must be secured to the vessel to assure proper flow velocity measurements. There is a great advantage of being able to remove the probe after implantation during surgery without resorting to additional surgical procedure.

The objective of a removable flow probe which gives reliable monitoring data of a vessel has been sought by suturing, embedding or attaching the probe directly to the vessel or associated outer tissue. The removal of the probe involved pulling lead wires or other lines from the probe to pull out the probe attachment. This can damage tissue including the grafted vessel or vessel which was monitored.

For example probes have been sutured to be adventitia, the layer of tissue on the outside of a vessel, and removed by pulling on the suture and probe. Payen, D. et al, "Comparison of Preoperative and Postoperative Phasic Blood Flow in Aortocoronary Venous Bypass Grafts by Means of Pulsed Doppler Echocardiography with Implantable Microprobes," Circ; Vol. 74. (Suppl. III), pp. 61–67 (1986); Svenning, J. L. et al, "Continuous Monitoring of Cardiac Output Postoperatively Using an Implantable Doppler Probe," Scand. J. Thor. Cardiovasc. Surg., Vol. 20, pp. 145–149 (1986). Another example, shown in Baudino, U.S. Pat. No. 4,541,433 issued Sept. 17, 1985, is a Doppler sensor with small metal tines in the tip of the probe. The tines are embedded in the adventitia. The device is removed by pulling on the probe so the tines are withdrawn from the adventitia.

The extractable, implantable probes of prior inventions must be attached loosely so that removal can be achieved. A loose attachment causes the potential for positional instability. The alignment of the probe must be stable in order to properly measure the flow through the vessel. Also, suturing and puncturing techniques used with probe attachment are potentially traumatic to the vessel. Suturing is potentially traumatic especially to a small vessel.

SUMMARY OF THE INVENTION

This invention is an implantable, extractable probe which has stable attachment to different sizes of vessels and is safely and easily removed from the patient. The probe can be used to monitor blood flow in connection with vascular surgery and in evaluation of vascular patency, blood flow and variations, cardiac output and drug responsiveness.

In addition to the blood flow probes this invention can be utilized with other biological sensors to monitor pressure, oxygen, temperature and the like. The probe body is adaptable to accommodate small sensor devices and can accommodate more than one sensor.

The body of the probe is made preferably of a biocompatible flexible rubber sheeting such as silicon rubber or other material which is not reactive to body tissue and fluids. The probe is generally a rectangular band sized large enough to encircle the vessel. A reinforcement fabric layer can be used. The combination of the rubber sheeting and fabric reinforcement provides a probe with some stretch when wrapped around the vessel to allow for vessel expansion.

The blood flow sensor can be a single or multiple piezoelectric crystals which are connected through lead wires from the probe to an instrument measuring blood velocity and vessel diameter. Each crystal is set preferably at about a 30° to about 60° angle within the probe with 45° sideways as the optimum for measuring the flow.

A flexible tube is attached to and communicates through one end to the body of the probe. The lead wires attached to either side of the crystal extend through the flexible tube and terminate at connections for the monitoring display instrument. A tractable release cable, wire or other tractable member also extends through the flexible tube and terminates inside the body of the probe.

A suture is held in place by the tractable member extending outside the probe body. The trailing ends of the suture extend through an opening outside the probe body. On the body opposite the flexible tubing suture guides or eyelets may be placed.

The vessel to be monitored is encircled with body of the probe. The suture is tied through the end of the probe and tightened so that the probe is firmly held around the vessel. During the attachment process no tissue penetration occurs. The flexible tubing extends outside the patient's body through the skin.

To release the probe, the tractable member outside the patient's body is pulled with gentle traction to partially withdraw it from inside the probe body. The movement of the portion of the member holding the suture inside the body of the probe causes the suture to be released. The probe unwinds from around the vessel. With further gentle traction the probe is extracted from the body.

BRIEF DESCRIPTION OF THE DRAWINGS

FIG. 1a is a detail of FIG. 1 showing a single suture thread embodiment.

FIG. 1b is a detail of the same area as FIG. 1a showing an alternative double suture embodiment.

FIGS. 5, 6, 7, 8 and 9 show the attachment of the probe body to a vessel.

DESCRIPTION OF THE PREFERRED EMBODIMENT

Figure 1:
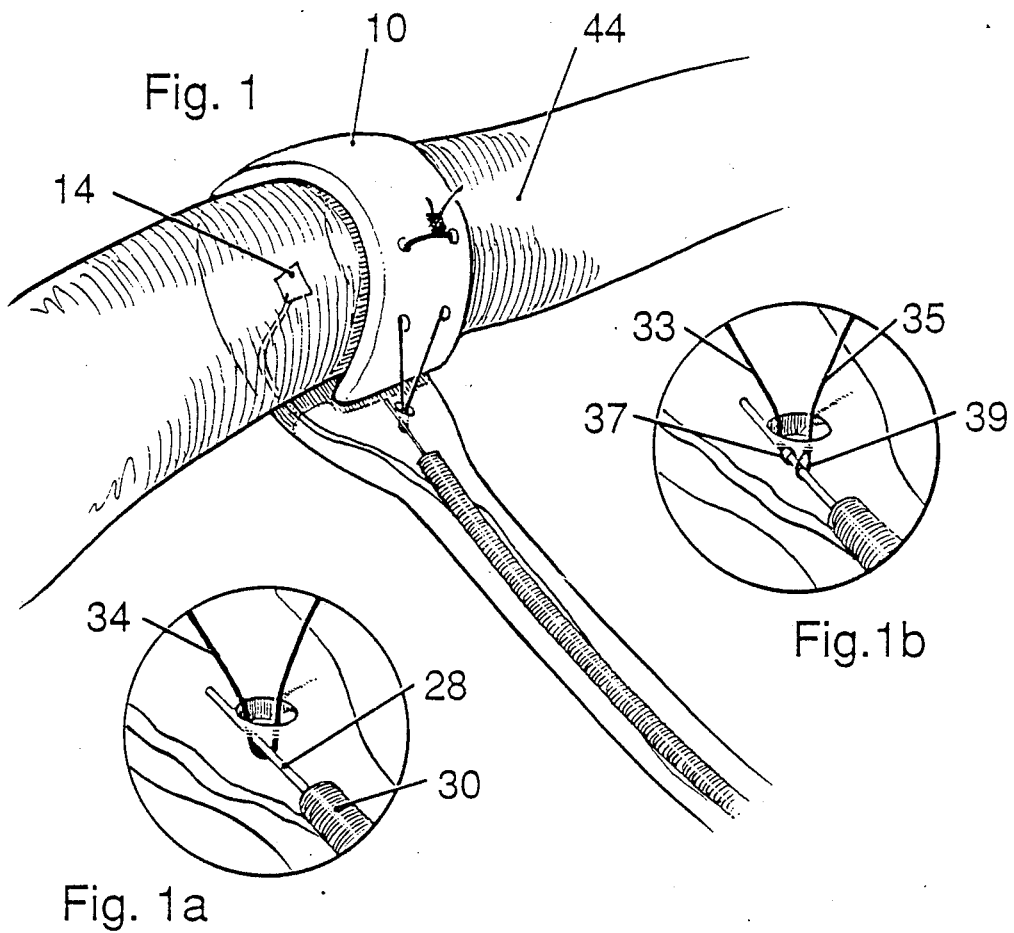
FIG. 1 is a perspective view in partial transparency of the installed probe around a vessel.

FIG. 1 is a view of the installed probe in partial transparency. The probe body 10 encircles the vessel 44 without overlap. Crystal 14 is aligned to read through the entire diameter of the vessel.

Figure 2:
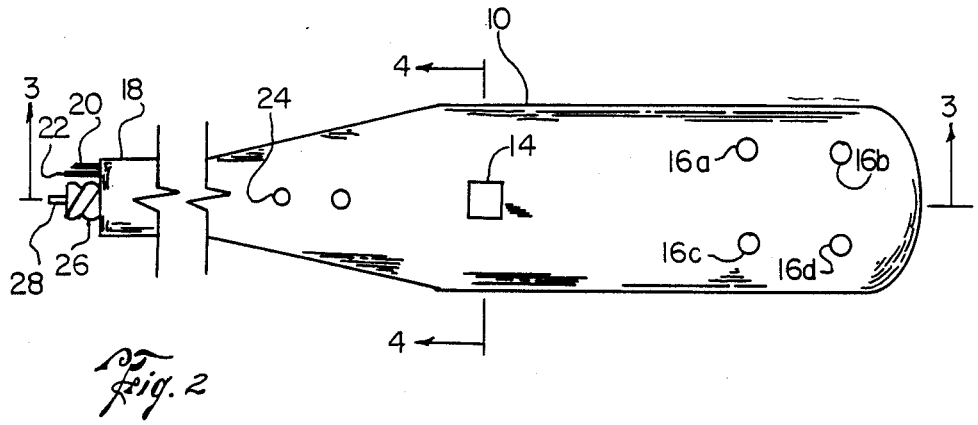
FIG. 2 is a top view of the probe body.

On one end of the probe body 10 of the preferred embodiment are suture guides 16a, 16b, 16c, and 16d as shown in FIG. 2. The suture guides are generally parallel pairs of perforations through the probe body. An embodiment can have a plurality of suture guides spaced in pairs along one end of the probe body 10. Depending on the length of probe desired to wrap around the vessel, the probe can be cut leaving suture guides at the end of the probe body to be used in the attachment process. As an example in the preferred embodiment, a blood flow sensor Doppler transducer crystal 14 is used. In FIG. 2 lead wires 20 and 22 are shown attached to crystal 14 and extending across the top of the probe body 10 into opening 24 going inside the probe body.

Figure 3:
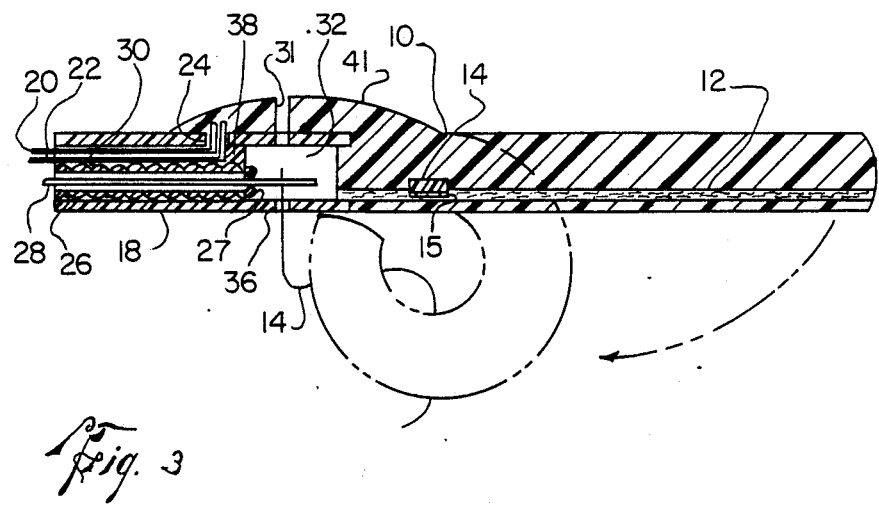
FIG. 3 is a length-wise section of the probe body at lines 3—3 of FIG. 2.

FIG. 3 is a section lengthwise through the probe. The probe body 10 is a generally rectangular body of flexible rubber sheeting which can be wrapped around a vessel. The rubber sheeting material is biocompatible such as silicon rubber which is not reactive to body tissue and fluids. The length of the probe body 10 is sized to encircle or partially encircle the vessel to be monitored. In an alternative embodiment the probe body is lengthened and cut to the appropriate size to surround the vessel to be monitored.

The probe body can be reinforced with a layer of fabric 12. The rubber probe body 10 and the fabric reinforcement 12 stretch to accompany vessel enlargement as needed. Other reinforcing materials similar to woven fabric can be used.

Figure 4:
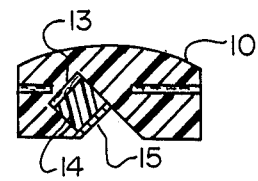
FIG. 4 is a cross-section of the probe body at lines 4—4 of FIG. 2.

A generally flat piezoelectric crystal 14 is embedded at the angle of about 30° to 60° sideways to the surface of the probe body that faces the vessel after attachment as further described. The crystal 14 is typically 10 MHz or 20 MHz but any frequency can be used. The face of the crystal 14 which faces the vessels has a thin coating 15 of epoxy for protection. On the other face of the crystal 14 is a layer 13 of acoustic material such as cork for sound absorbency. FIG. 4 shows the orientation of crystal 14 in the probe body at an angle. Although the preferred embodiment drawings are of a Doppler crystal, any type of miniature biological sensor can be utilized in this invention.

On the end of probe body 10 opposite the suture guides extends tube 18 of flexible material such as silicon rubber. The crystal 14 is embedded between the tube 18 and the suture guides 16a, 16b, 16c and 16d as shown in FIGS. 2 and 3. Lead wires 20 and 22 are soldered one to each face of crystal 14. Other lead wire configurations may be used depending on the sensor used. The lead wires 20 and 22 extend from crystal 14 and further extend into tube 18 through a small opening 24 near the connection of tube 18 with probe body 10. The lead wires 20 and 22 extend through the length of tube 18 and ultimately terminate at connections for a monitoring display instrument which reads the signals from the biological sensor.

A release cable 26 extends through the tube 18. In FIGS. 2 and 3 the release cable shown is a steel wire 28 at least partially surrounded by a wire coil 30. The release cable 26 is flexible. In FIG. 3 the steel wire 28 extends into the probe body 10 in a cavity 32 situated between the tube attachment to the probe body and the crystal 14. In FIG. 1 the steel wire 28 which extends into the cavity 32 is not wrapped with the wire coil 30. Generally the cavity is adjacent the tube entrance so that the steel wire 28 easily extends into the cavity. In a longer probe embodiment the crystal would be further spaced from the cavity.

The suture used to hold the probe in place is shown in two embodiments in enlargements FIG. 1a and FIG. 1b. In FIG. 1a a suture 34 is looped around the part of steel wire 28 which extends into the cavity 32. The free ends of suture 34 extend outside the probe body through an opening 36 in the bottom of the probe body 10 which communicates with the cavity 32. An opening 31 is made through the top of the probe body into the cavity near the suture 34. By use of openings 31 and 36 additional sutures can be placed after the probe has been used and the original sutures have been discarded. The probe can be reused.

In FIG. 1b two separate sutures 33 and 35 are individually looped at one end and the loops 37 and 39 respectively are slipped over the steel wire 28 inside cavity 32. The free end of both suture 33 and 35 extend outside the probe body in the similar manner as suture 34. In both embodiments there are two threads extending from the probe body for use in attaching the probe. For illustration purposes the embodiment in FIG. 1a is used for the rest of the drawings although either suture embodiment may be used.

In FIG. 3 the release cable 26 is fixed at about the point of joinder of flexible tube 18 and probe body 10 near the cavity 32 by an inner layer 38 of rubber surrounding the release cable 26 and filling the internal diameter of tube 18. The release cable 26 is positioned inside the tube 18 so that the portion of steel wire 28 with the looped suture 34 is held in place in the cavity 32. A seal 27 of rubber or other material is placed between the outer wire coil 30 and the stainless steel wire 28 to prevent entrance of foreign material inside the coil. Also, the cavity 32 may be filled with a substance that will allow the traction of steel wire 28.

An outer coating 41 of silicon rubber covers the top of the probe body 10 enclosing and protecting the lead wires 20 and 22 which extend from crystal 14 into the tubing 18.

The FIGS. 5, 6, 7, 8 and 9 illustrate the attachment of the probe to a vessel. In the Figures some parts of the probe are shown in more relative transparency so that the operation can be easily viewed.

In FIG. 5 the vessel to be monitored has been located and the section of the vessel 44 for probe attachment has been isolated and if necessary dissected. As shown in FIG. 6, the surgeon inserts the probe body 10 under and around the vessel. The free ends of the suture 34 terminate in curved needles 40 and 42. The loop of suture on steel wire 28 inside the probe body 10 is shown and the free ends of the suture extend through opening 36. Tube 18 is long enough to extend outside the patient's body through an opening in the skin.

Further in the process in FIG. 7 the two free ends of the suture 34 are looped under the vessel. The suture needle 42 is inserted through suture guides 16b and 16a and needle 40 is inserted through suture guides 16d and 16c to thread the two ends of suture 34 to the end of probe body 10. Suture guides are not necessary as the suture needles can generally penetrate the flexible sheeting material of the probe body 10. As shown in FIG. 7 the suturing process can be done away from the vessel 44 enabling the surgeon to easily manipulate the probe without damage to the vessel or necessitating close work near the vessel. The installation of the probe is simplified in this manner.

Figure 11A:
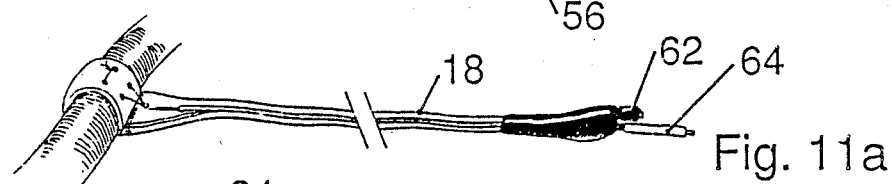
FIGS. 11a, 11b and 11c show the probe release process.
Figure 11B:
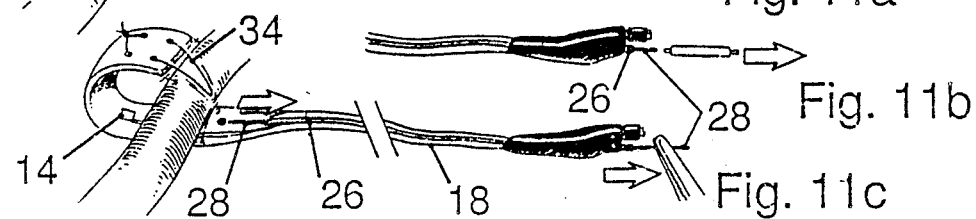
Figure 11C:
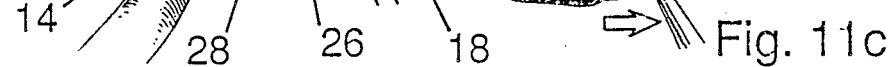

FIG. 8 shows the drawing up of the sutures after threading through the suture guides. As shown in FIG. 8 the suture does not go underneath the probe body 10 so that release will be achieved as shown in FIGS. 11a, 11b and 11c. The dual suture arrangement of FIG. 1b will allow for the suture to go underneath the probe and release according to this invention. As the sutures are tightened the probe body 10 wraps around the vessel. The crystal 14 is positioned at the vessel wall so that a sound beam travels across the lumen of the vessel approximately through the center line. FIG. 9 shows the probe body 10 encircling the vessel after the suture has been tightened, tied and in the process of having the free ends cut.

FIG. 1 is a transparency showing the crystal 14 positioned snugly next to the vessel with the probe body suture in place around the vessel. The suture opening 36 is spaced on the end of the probe body opposite the suture guides as shown so that when the probe is tightened, it encircles the vessel without overlap. It is possible to use a probe which partially encircles the vessel as long as the crystal is positioned properly. FIG. 1 shows the probe as it would remain in the patient's body for a period of time.

Figure 10:
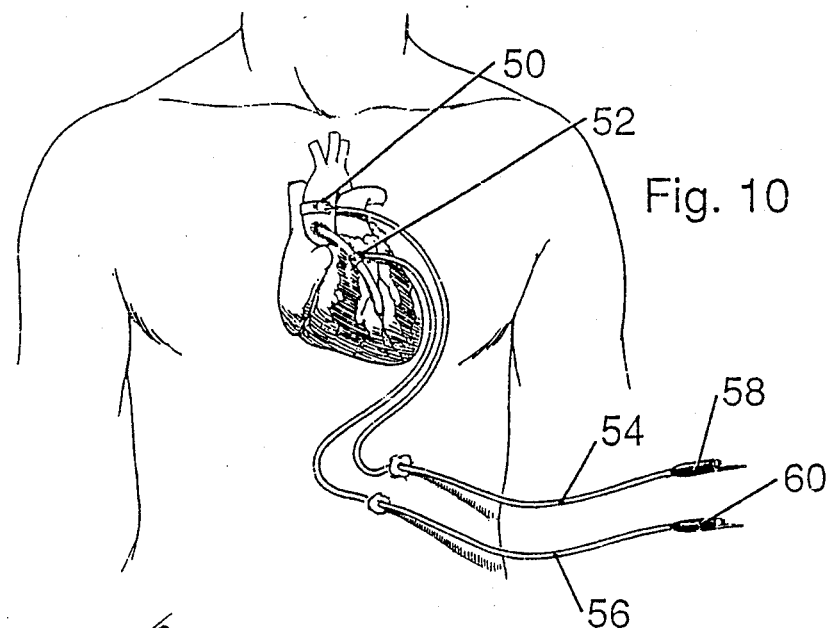
FIG. 10 shows two sizes of probes used in a patient.

FIG. 10 is illustrative of the use of probes in a patient and shows two sizes. Probe 50 is a longer version monitoring the aorta. Probe 52 is a shorter version monitoring a grafted vessel. The flexible tubes 54 and 56 extend from the probe bodies 50 and 52 respectively and terminate in connections 58 and 60 which plug into display monitors. The release cables also extend through the terminal ends of tubes 54 and 56.

FIGS. 11a, 11b and 11c illustrate the nonsurgical removal procedure of the probe. The release cable 26 extends through the tube 18 as well as the lead wires 20 and 22. The lead wires are fitted to a connection 62 for the display monitor (not shown). The end of the release cable 26 is covered by a cap 64 for protection to assure that the release mechanism is not accidently actuated.

The cap 64 is removed, as shown in FIG. 11b, when the probe is to be removed from the body. A portion of the steel wire 28 of the release cable 26 extends outside of the wire coil 30. The steel wire 28 is tractable independently of the coil 30. In FIG. 11c a needle holder grasps the end of steel wire 28 with gentle traction. The traction on the steel wire 28 causes it to move from its position in cavity 32 securing the looped suture 34. With the movement of steel wire 28 from inside cavity 32 the suture is released from the probe body. The probe can unwind from around the vessel. The release is shown in FIG. 11c. Generally when the probe is released the output from the biological sensor will cease or change due to a change in position of the probe. The probe is then extracted.

Figure 12:
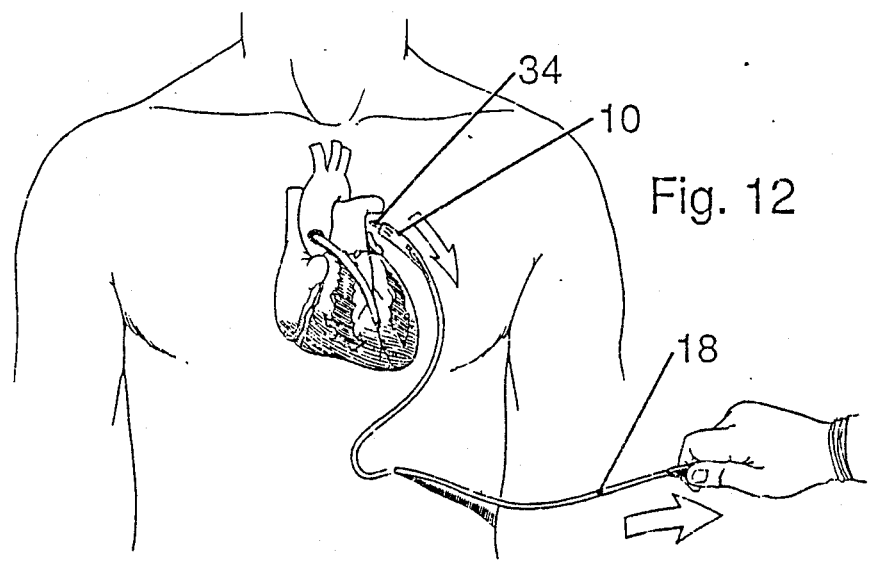
FIG. 12 shows the extraction of the probe from the body.

Further traction on the tube 18 will pull the probe out of the patient's body as shown in FIG. 12. The tube can be pulled gently and the device removed without surgery through the opening in the skin through which the tube extended. The probe can be extracted at any time with the release device of this invention.

Figure 13:
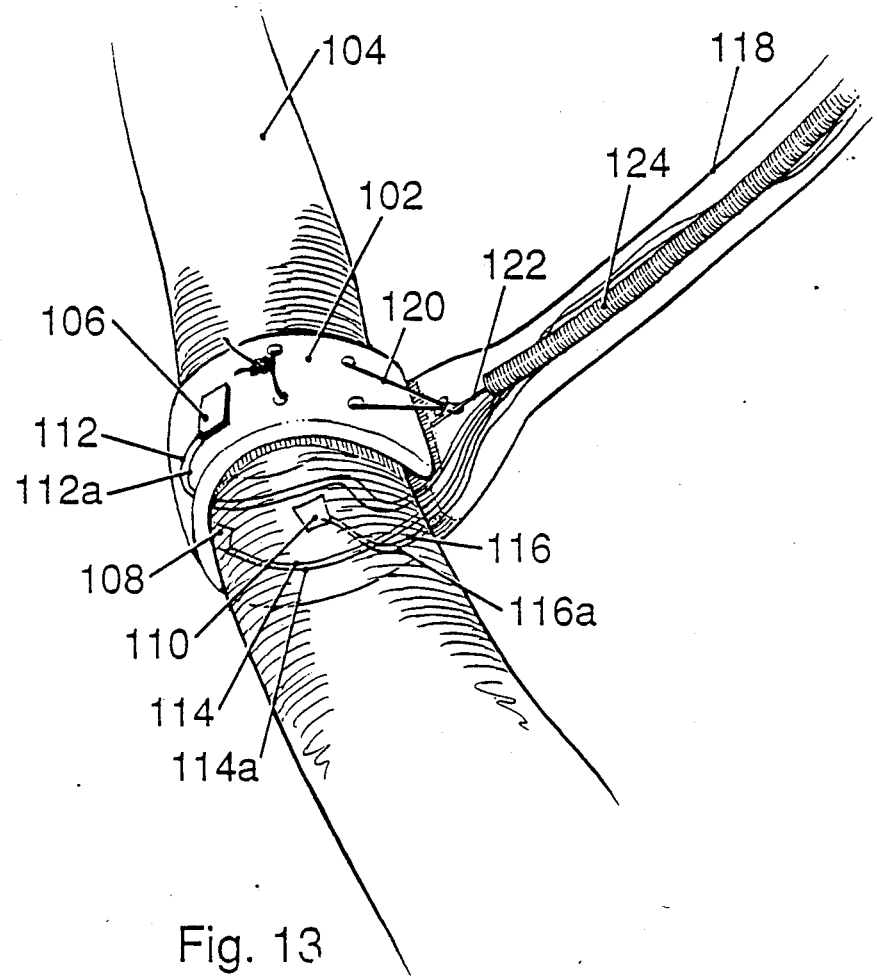
FIG. 13 shows an alternative embodiment with multiple sensors in the probe.

FIG. 13 is an alternative embodiment showing multiple crystals embedded in a probe body. For illustrative purposes probe body 102 is shown encircling vessel 104. Biological sensors 106, 108 and 110 are shown in transparency in probe body 102 spaced between the terminal end of the probe body and flexible tubing 118 extending from the probe body 102. With the exception of the multiple sensors the probe body 102 and suturing and tractable release members are as described above for FIGS. 1-12. In FIG. 13 the sensors 106, 108, and 110 are shown with associated pairs of lead wires 112 and 112a, 114 and 114a, and 116 and 116a, respectively. The lead wires extend from the sensors through flexible tube 118.

The probe is shown in the sutured state with suture 120 wrapped around steel wire 122. Cable 124 encloses the steel wire 122 past the suture and extends through the flexible tubing 118. The implantation and release methods are the same as described above.

The multiple sensor embodiment can be utilized in a variety of circumstances. More than one type of biological sensor can be placed in the probe. In the case of Doppler transducers, more than one crystal in the probe can provide increased assurance of correct orientation by one or more of the crystals for accurate flow measurements. Multiple crystals also are protection in case of malfunction of one crystal. Multiple crystals give more than one sampling of data for comparison purposes.

In the case of some vessels such as the aorta, there is a nonsymmetric velocity profile. A multiple crystal probe is preferable to give a profile of nonsymmetric flow. The sensors can be run in sequence or simultaneously as desired. Other uses of the single and multiple sensor probe are evident from this disclosure. The claimed invention is intended to include all uses.

What is claimed is:
1. An implantable and extractable probe comprising:
   at least one biological sensor;
   lead wires extending from said sensor;
   a flexible band to which said sensor is fixed;
   a suture means terminating in ends;
   means for retaining part of the suture means inside the flexible band with the ends of the suture means extending outside the band; and
   means for selectively releasing the part of the suture means head inside said flexible band.
2. An implantable and extractable probe comprising:
   at least one biological sensor;
   lead wires extending from said sensor;
   a flexible band of material to which said sensor is fixed;
   a cable at least partially within said flexible band extending outside of said band;
   means for at least partial withdrawal of said cable from within said flexible band; and
   a suture looped over said able within said flexible band, the suture having ends which extend outside said band.

3. An implantable and extractable probe of claim 2 wherein said flexible band is a generally rectangular shaped biocompatible material.

4. An implantable and extractable probe of claim. 2 wherein said flexible band of material has suture guides opposite to the end from the cable extension.

5. An implantable and extractable probe comprising:
at least one biological sensor;
lead wires extending from said sensor;
a flexible band to which said sensor is fixed;
a suture means;
a retainer for the suture means inside the flexible band with ends of the suture means extending outside the band; and
a means for releasing the retainer of the suture means said means external of the flexible band.

6. An implantable and extractable probe of claim 5 wherein said means for releasing the retainer is a retractable member which holds the suture means inside the band and upon a traction releases the suture means.

7. An implantable and extractable probe in a flexible band comprising:
at least one biological sensor;
a generally rectangular flexible band of biocompatible material sized to surround a vessel with said probe fixed therein;
a sufficient number of suture guides on one end of said flexible band;
a flexible tube extending from the end of said band opposite to said suture guides;
lead wires from said probe extending through said flexible tube;
a cable extending through said flexible tube into a length of a cavity formed adjacent to said probe inside of said flexible band;
a suture means terminating in ends placed around the portion of said cable in said cavity inside of said flexible band and the ends of the suture extending outside of the flexible band through an opening communicating with said cavity; and
means for selectively withdrawing said cable outwardly from the cavity to release the suture placement around said cable.

8. An implantable and extractable probe of claim 7 wherein said flexible band has a fabric reinforcement layer.

9. An implantable and extractable probe of claim 7 wherein said flexible band has an extended length containing multiple suture guides at preselected spacing.

10. An implantable and extractable probe of claim 7 wherein said biological sensor is a blood vessel flow velocity sensor.

11. An implantable and extractable probe comprising:
at least one biological sensor;
lead wires extending from said sensor;
a flexible band to which said sensor is fixed;
a cable at least partially within said flexible band extending outside of said band;
means for at least partial withdrawal of said cable from within said flexible band; and
more than one suture with an end of each forming a loop around said cable and an opposite end extending outside said band.

12. A blood vessel flow probe comprising:
at least one Doppler transducer;
a generally rectangular flexible silicon rubber sheeting body sized to wrap lengthwise around a vessel with said transducer embedded in the rubber sheeting body which has a facing orientation on one side of said sheeting body to face a vessel after the sheeting is wrapped around the vessel;
a fabric reinforcement layer included in said rubber sheeting body;
a flexible tube extending from one end of the rubber sheeting body;
a sufficient number of suture eyelets for suture attachment on an end of the rubber sheeting body opposite to the flexible tube;
a release cable of a central steel wire partially surrounded by a wire coil with one end of the steel wire not surrounded by the wire coil extending into a cavity adjacent said probe and said release cable enclosed in said flexible tube which communicates on one end with said cavity;
a suture means terminating in ends placed around said steel wire in the cavity with the suture ends extending out of said rubber sheeting body through a perforation communicating into said cavity with said perforation on the same side of said rubber sheeting body as the facing orientation of the Doppler transducer; and,
lead wires associated with said probe extending 13. A blood vessel flow probe of claim 12 wherein said Doppler transducer is a crystal embedded at an angle of between 30° and about 60° sideways inside said rubber sheeting body.

* * * * *